United States Patent [19]

Chambers et al.

[11] Patent Number: 5,717,086
[45] Date of Patent: Feb. 10, 1998

[54] PREPARATION OF FLUORO-NUCLEOSIDES AND INTERMEDIATES FOR USE THEREIN

[75] Inventors: Owen Ross Chambers; Patrick Charles Youmans, both of Bristol; Andrew Lawrence Germain, Kent, all of United Kingdom

[73] Assignees: Rhone-Poulenc Chemicals Limited, Hertfordshire; The Wellcome Foundation Limited, London, both of United Kingdom

[21] Appl. No.: 545,842

[22] PCT Filed: May 12, 1994

[86] PCT No.: PCT/GB94/01024

§ 371 Date: Feb. 14, 1996

§ 102(e) Date: Feb. 14, 1996

[87] PCT Pub. No.: WO94/26762

PCT Pub. Date: Nov. 24, 1994

[30] Foreign Application Priority Data

May 12, 1993 [GB] United Kingdom ............... 9309794
Sep. 13, 1993 [GB] United Kingdom ............... 9318914

[51] Int. Cl.$^6$ .................................................. C07H 19/06
[52] U.S. Cl. .................. 536/27.11; 536/28.2; 536/28.53; 514/50
[58] Field of Search .................. 536/27.11, 28.53, 536/28.2

[56] References Cited

U.S. PATENT DOCUMENTS

| | | | |
|---|---|---|---|
| 5,153,180 | 10/1992 | Matthes et al. | 514/50 |
| 5,157,114 | 10/1992 | Rahim et al. | 536/28.54 |
| 5,223,263 | 6/1993 | Hostetler et al. | 424/450 |
| 5,376,644 | 12/1994 | Selway et al. | 514/50 |
| 5,449,664 | 9/1995 | Verheyden et al. | 514/45 |
| 5,574,149 | 11/1996 | Van Tuttle et al. | 514/50 |

FOREIGN PATENT DOCUMENTS

| | | |
|---|---|---|
| 0 356 166 | 2/1990 | European Pat. Off. . |
| 0 470 355 | 2/1992 | European Pat. Off. . |
| 0 495 225 | 7/1992 | European Pat. Off. . |
| 91 06554 | 5/1991 | WIPO . |

OTHER PUBLICATIONS

Morisawa et al., "3-Deoxy-3-fluoro-5-substituted-D-ribofuranoside Derivative as Antitumor Agents and Virucide," Japanese Kokai Tokkyo Koho JP 02 96,950 [90 96,950], published 9 Apr. 1990; Chem. Abstr., 113(13), p. 743, Abstr. No. 115, 782a 1990); only abstract supplied.

Szabolcs et al., "Preparation of (5-Substituted) 3'-azido-2', 3'-dideoxyribonucleosides," Hungarian Patent Document HU 48,901, published 29 Jul. 1989; Chem. Abstr., 112(25), p. 670, Abstr. No. 235776c (1990); only abstract supplied.

Kowollik et al., "Nucleosides of Fluorinated Sugars. XII. Synthesis of 1-(2, 3-Dideoxy-3-fluoro-β-D-ribofuranosyl)pyrimidines." J. Prakt. Chem., 315(5), 895-900 (1973); Chem. Abstr., 80(9), p. 392, Abstr. No. 48302d (1974); only abstract supplied.

Joecks et al., "NMR Spectroscopic Studies of the Conformational Behavior of Some 2'-and 3'-Halogen-substituted Pyrimidine Nucleosides." J. Prakt. Chem., 325(6), 881-892 (1983); Chem. Abstract., 100(25), p. 644, Abstr. No. 210313p (1984); only abstract supplied.

Ueda, "Synthesis and Reaction of Pyrimidine Nucleosides," Ch. 1 in Chejmistry of Nucleosides and Nucleotides, vol. 1, Townsend (ed.), Plenum Press, New York, NY, 1988, pp. 1-112, only pp. 1, 53, 61-62 and 105-106 supplied.

Balzarini et al., "[]," Biochemical Pharmacology, 37(), 2847-[] (1988).

Herdewijn et al. "[]," Nucleosides & Nucleotides. 8(), 65-[] (1989).

Journal of Medicinal Chemistry, vol. 32, No. 8, Aug. 1989, pp. 1743-1749, A. Van Aerschot et al., "'3'-Fluoro-2', 3'-dideoxy-5-chlorouridine: Most Selective Anti-HIV-1 Agent Among a Series of New 2'- and 3'-Fluorinated 2', 3'-Dideoxyucleoside Analogues".

Chemical Abstracts, vol. 113, No. 13, Sep. 24, 1990, Y. Morisawa et al, "'3-Deoxy-3-fluoro-5-substituted-D-ribofuranoside Derivatives as Antitumour Agents and Virucides", p. 743, col. 1, Apr. 1990.

Chemical Abstracts, vol. 112, No. 25, Sep. 18, 1990, Szabolcs et al., "Preparation of (5-Substituted) 3'-Azido-2', 3'-Dideoxyribonucleosides", p. 670, col. 2.

Chemical Abstracts, vol. 80, No. 9, Mar. 4, 1974, Kowollik et al, "Nucleosides of Fluorinated Sugars. XII. Synthesis of 1-(2,3-Dideoxy-3-Fluoro-beta-D-ribofuranosyl) Pyrimidines", p. 392, col. 2.

Chemical Abstracts, vol. 100, No. 25, Jun. 18, 1984, Joecks et al, "NMR Spectroscopic Studies of the Conformational Behavior of Some 2'- and 3'-Halogen Substituted Pyrimidine Nucleosides", p. 644, col. 1.

Journal of Medicinal Chemistry, vol. 33, No. 2, Feb. 1990, pp. 845-848, Hiebl et al, "Synthesis, Antiretrvirus Effects and Phosphorylation Kinetics of 3'-Isocyano-3'-Deoxythymidine and 3'-Isocyano-2', 3'-Dideoxyuridine".

Primary Examiner—John Kight
Assistant Examiner—L. Eric Crane
Attorney, Agent, or Firm—Burns, Doane, Swecker & Mathis, L.L.P.

[57] ABSTRACT

2',3'-Dideoxy-3'-fluorouridines are made by reaction of a corresponding anhydronucleoside with hydrogen fluoride in the presence of an organo-iron compound.

15 Claims, No Drawings

PREPARATION OF FLUORO-NUCLEOSIDES AND INTERMEDIATES FOR USE THEREIN

This invention relates to the preparation of 2',3'-dideoxy-3'-fluorouridine, and intermediates for use therein.

Certain substituted 2',3'-dideoxy ribonucleosides are known inhibitors of reverse transcriptase activity and are of potential importance in the treatment of diseases caused by retroviruses, including HIV. 3'-Fluoro-2',3'-dideoxyuridine is an intermediate in the preparation of therapeutically useful 2',3'-dideoxy-ribonucleosides, disclosed in, for example, EP-A-305117 and 356166 (The Wellcome Foundation Limited).

European Specification EP-A-0470355 describes inter alia a process for the preparation of 3'-fluoro-2',3'-dideoxy-nucleosides by reaction of a corresponding anhydro dideoxy-nucleoside with hydrogen fluoride in the presence of an aluminium-containing catalyst. The catalyst may be, for example, aluminium acetylacetonate.

East German Specification 103241 describes the preparation of 3'-fluoro-2',3'-dideoxyuridine by reaction of the corresponding 5-O-mesyl-anhydronucleoside with hydrogen fluoride in the presence of an aluminium fluoride catalyst, followed by removal of the mesyl group.

The use of aluminium-containing compounds in the preparation of drugs has attracted unfavourable criticism because of the possible involvement of aluminium in the etiology of Alzheimer's disease. It is therefore desirable to provide catalysts for the aforesaid reaction which do not contain aluminium. There is also a general need for catalysts which give a more rapid reaction and/or a higher yield of the desired product.

It has now been found that certain iron compounds are highly effective catalysts in the aforesaid reaction and give more particularly a higher reaction yield and/or a shorter reaction time than the corresponding aluminium compound.

The present invention accordingly provides a process for the preparation of a nucleoside of formula:

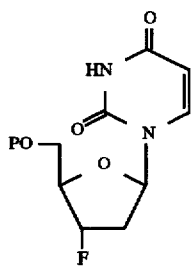

(I)

where P is hydrogen or a hydroxy-protecting group, which comprises reacting an anhydronucleoside of formula:

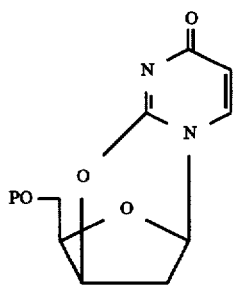

(II)

where P is as hereinbefore defined, with hydrogen fluoride under anhydrous conditions in the presence of an organo-iron (III) compound of formula:

$$FeY_mZ_n \quad \text{(III)}$$

where Y is a monodentate ligand, Z is a bidentate ligand and m and n are each zero or positive integers such that (m+2n)=6, and optionally replacing a hydroxy-protecting group P by hydrogen.

In the starting material of formula II the 5'-hydroxyl radical may be unprotected (i.e. P may be hydrogen), but preferably it is protected by a radical which can be readily removed after the reaction to liberate the hydroxyl radical. A variety of suitable radicals are available for this purpose and their introduction into the starting material and subsequent removal after the reaction are well known to those of ordinary skill in this art. P may be, for example, an acyl group such as $C_{1-6}$ alkanoyl, e.g. acetyl or pivaloyl, or an aroyl group optionally substituted by $C_{1-4}$ alkoxy or nitro, e.g. benzoyl, 2-naphthoyl, 4-methoxybenzoyl, 4-nitrobenzoyl, or 3,5-dinitrobenzoyl, an ether group such as tri-$C_{1-6}$ alkylsilyl, e.g. trimethylsilyl, an aralkyl group, e.g. benzyl or triphenylmethyl, or methanesulphonyl. The use of a 4-methoxybenzoyl radical is preferred.

The compounds of formulae (I) and (II) in which P is a branched chain alkanoyl of 4 to 6 carbon atoms, e.g. pivaloyl, benzoyl substituted by alkoxy of 1 to 4 carbon atoms or byl or 2 nitro radicals, e.g. 4-methoxybenzoyl, 4-nitrobenzoyl, or 3,5-dinitrobenzoyl, or 1- or 2-naphthoyl are new compounds and as such within the scope of the present invention. 2,3'-Anhydro-5'-(4-methoxybenzoyl)-2'-deoxyuridine and 2'3'-dideoxy-3'-fluoro-5'-(4-methyoxybenzoyl)uridine are especially valuable.

The reaction is carried out under anhydrous conditions and preferably in the presence of an inert organic solvent, preferably an aprotic solvent, e.g. 1,4-dioxane, tetrahydrofuran, 1,2-dimethoxyethane, or bis(2-methoxyethyl)ether. The use of 1,4-dioxane is preferred.

The organoiron compound of formula III may be any suitable derivative of iron which is at least partially soluble in the reaction medium. The ligand Y is preferably halogen (e.g. fluorine or chlorine) or alkoxy of 1 to 4 carbon atoms which may be halogenated (e.g. methoxy, ethoxy, isopropoxy or 2,2,2-trifluoroethoxy). The ligand Z is preferably a carboxylato radical derived from an alkanoic acid of up to 12 (preferably 1 to 6) carbon atoms which may be halogenated (e.g. acetic acid). Alternatively, the ligand Z may be β-diketo residue of a compound of formula R'-COCH$_2$CO-R" where R' is alkyl or haloalkyl (including perfluoroalkyl) of 1 to 4 carbon atoms (e.g. methyl) and R" is hydrogen, hydroxy, alkyl or haloalkyl (including perfluoroalkyl) of 1 to 4 carbon atoms, or alkoxy of 1 to 4 carbon atoms, and more especially methyl or ethoxy.

Preferred organo-iron compounds for use in the present invention are those in which m is preferably zero, n is preferably 3, and Z is preferably a β-diketo residue, e.g. acetylacetonato. The use of iron (III) acetylacetonate is especially preferred.

The proportions of the starting materials and organoiron compound are not critical. An excess of the hydrogen fluoride, e.g. from 2 to 20 moles per mole of anhydro nucleoside starting material, is generally used. The proportion of the organo-iron compound is generally approximately equimolar with the anhydro-nucleoside starting material, e.g. 0.5 to 2.0 moles of the organometallic compound (on the basis of its metal content) per mole of the anhydro-Aucleoside starting material.

The reaction is conveniently carried out with moderate heating, e.g. to 50° to 150° C. For higher temperatures within this range, the reaction vessel is preferably closed so that the reaction is carried out under autogenous pressure.

This makes possible the use of reaction temperatures greater than the boiling point at atmospheric pressure of the solvent used.

Because of the high activity of the organo-iron compounds used in the process of the present invention, the reaction times required are usually less than those necessary when an organo-aluminium compound is used. A reaction time of 0.5 to 4 hours is generally satisfactory.

The reaction mixture may be worked up in conventional manner. The excess hydrogen fluoride is preferably first removed, e.g. by reaction with calcium carbonate to give insoluble calcium fluoride or by reaction with potassium fluoride. The thus-insolubilized fluorine compounds are removed, e.g. by filtration, and dilution of the separated reaction medium with water causes the desired product to precipitate. It may then be separated, e.g. by filtration and purified in the usual way, but very often it is sufficiently pure for use in the next stage without additional purification.

Where a hydroxyl-protecting radical P is present in the product, it may be removed in conventional manner. For example, the preferred protecting radical 4-methoxybenzoyl may be removed by reacting the product with a solution of an alkali metal hydroxide in a lower alcohol, e.g. a solution of sodium hydroxide in methanol. This causes the 4-methoxybenzoyl radical to be removed in the form of its lower alkyl ester, e.g. methyl-4-methoxybenzoate. This ester precipitates and can easily be removed. Concentration of the separated reaction mixture then causes the desired product to separate out.

The anhydronucleosides of formula (II) may be prepared from a corresponding nucleoside of formula:

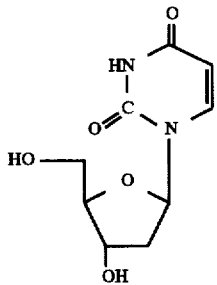

by reaction with a dehydrating agent, preferably in the presence of an acid of formula POH, where P is as hereinbefore defined. For example, 2'-deoxyuridine may be reacted with a combination of diisopropylazodicarboxylate or diethylazodicarboxylate and a triaryl- or trialkyl-phosphine or -phosphite, e.g. triphenylphosphine, preferably in the presence of the said acid, in an inert polar solvent, e.g. dimethylformamide, at a temperature in the range of 0° to 150° C., preferably 15° to 35° C., and usually at ambient temperature, using substantially equimolecular proportions of the reagents.

The following Examples illustrate the invention.

EXAMPLE 1—The Preparation of 2,3'-anhydro-5'-(4-methoxybenzoyl)-2'-deoxyuridine (AMBU)

Di-isopropylazodicarboxylate (131.3 g., 0.65 moles) was added dropwise over a 1 hour period to a stirred mixture of 2'-deoxyuridine (114.0 g., 0.5 moles), 4-methoxybenzoic acid (87.4 g., 0.58 moles), triphenylphosphine (166.4 g., 0.64 moles) and dimethylformamide (684 ml) while maintaining the temperature at 25°–29° C. with the aid of an ice-bath. On completion of the addition the mixture was stirred for a further 2 hours and then a second portion of triphenylphosphine (166.4 g., 0.64 moles) was added and stirred until dissolved. A second portion of di-isopropylazodicarboxylate (131.3 g., 0.65 moles), was then added dropwise while continuing to maintain the temperature in the range 25°–29° C. with ice bath cooling. On completion of the addition, the mixture was stirred at this temperature for a further hour and then the precipitated product collected by filtration. The filter cake was sucked free of DMF, washed with ethanol (3 washes of 114 ml), and dried at 80° C. under vacuum. The yield obtained was 132 g (77% of theoretical).

A 10 g sample of the crude AMBU was purified by recrystallisation from four volumes of 20% aqueous acetonitrile. The product was collected by vacuum filtration and dried for 12 hours at 80° C. yielding 8.9 g (89% return).

EXAMPLE 2 (Comparative)—The Preparation of 2',3'-dideoxy-3'-fluoro-5'-(4-methoxybenzoyl) uridine (MOB-3') in the absence of a metal complex 1,4-Dioxane (350.0 g., 4.0 moles) was transferred from a metal cylinder (under nitrogen) via a calibrated, glass measuring cylinder to a magnetically stirred, 2 litre polypropylene flask. Anhydrous hydrogen fluoride (13.6 g., 0.58 moles) was then taken from a metal cylinder via a calibrated sight glass and bubbled into the dioxane with continuous stirring.

Into a 1 litre stirred monel, autoclave was charged 2,3'-anhydro-5'-O-(4-methoxybenzoyl)uridine (AMBU)(20.2 g., 0.059 moles). This was carried out under nitrogen to prevent the absorption of moisture. The previously prepared HF/dioxane mixture was then passed with nitrogen into the autoclave. The stirred mixture was then heated to 110° C. over 30 minutes.

The reaction was sampled over a 3 hour reaction time by bleeding out small (ca. 0.2 g) samples into 5 ml plastic vials containing deionised water (1 ml). The samples were neutralised with calcium carbonate, and ethyl acetate (ca. 1 ml) was added. The samples were then spun at 3000 rpm on a centrifuge for 5 minutes. The top organic layer was removed using a teat pipette and analyzed by HPLC.

After 30 minutes, the sample analysis indicated that the product constituted only 20% of the nucleosides present. This did not increase over the subsequent 2½ hours.

EXAMPLE 3(Comparative)—The Preparation of 2',3'-Dideoxy-3'-fluoro-5'-(4-methoxybenzoyl) uridine (MOB-3') in the presence of aluminium acetylacetonate 2',3'-Anhydro-5'-O-(4-methoxybenzoyl)uridine (AMBU) (19.8 g., 0.057 moles) and aluminium acetylacetonate (15.8 g., 0.049 moles) were charged into a 1 litre monel autoclave, fitted with a mechanical stirrer. The charging to the autoclave was carried out under nitrogen. 1,4-Dioxane (351.2 g., 4 moles) was charged under nitrogen to a litre polypropylene flask, fitted with a magnetic stirrer. Anhydrous hydrogen fluoride (9.31 g., 0.47 moles) was then transferred under nitrogen into the dioxane with continuous stirring. The reaction mixture was then heated to 95° C. over a period of 30 minutes.

The reaction mixture was sampled over a 5 hour reaction period. Small samples (ca. 0.2 g.) were bled from the autoclave into 5 ml plastic vials containing deionised water (1 ml). The samples were neutralised by adding calcium carbonate, and ethyl acetate was then added. The sample was then spun at 3000 rpm for 5 minutes on a centrifuge, and the top organic layer was analyzed by HPLC. After 30 minutes, the sample analysis indicated that the MOB-3' constituted 60% of the nucleosides present with 25% of unreacted AMBU. After 2 hours, no further reaction was observed and the MOB-3' constituted 88% of the nucleoside present. After the 5 hour reaction period, the reaction mixture was cooled and filtered through a plastic Büchner funnel to remove a solid residue (24.6 g). Deionised water (769.7 g) was added to the filtrate (290.3 g), which resulted in a white precipitate. The white precipitate was then filtered off, washed with ice cold methanol (49.6 g) and dried in a vacuum oven. The dried product (7.2 g) assayed as 100.1% w/w by HPLC, i.e. a reaction yield of 34.2%.

The aqueous filtrate obtained after removing the precipitated product was further treated. Initially, further deionised water (121 g) was added but no further precipitation was observed. It was then neutralised (pH 4–5) with calcium carbonate (49.2 g, 0.5 m) and extracted with ethyl acetate (600 g). The inorganics were removed by filtration and the filtrate was phase separated. The organic phase was stripped on a rotary evaporator to yield a sticky solid. Methanol (30 g) was added and the off-white solid was filtered off and dried. The dry solid (4.1 g) was assayed by HPLC as 95.6% w/w MOB-3', i.e. a further reaction yield of 18.7%.

The total reaction yield was thus 52.9%.

EXAMPLE 4—The Preparation of 2',3'-Dideoxy-3'-fluoro-5'-(4-methoxybenzoyl) uridine (MOB-3') in the presence of iron (III) acetylacetonate Into a 1 litre monel autoclave, fitted with a mechanical stirrer, was placed 2',3'-anhydro-5'-O-(4-methoxybenzoyl) uridine (AMBU)(20.7 g, 0.060 moles) and iron (III) acetylacetonate (20.8 g, 0.059 moles), the charging being carried out under nitrogen. Dioxane (360 g, 4.1 moles) and anhydrous hydrogen fluoride (8.8 g, 0.44 moles) wee then mixed as previously described (see Example 2), and charged to the autoclave. The reaction mixture was then heated to 95° C. over 30 minutes.

The reaction mixture was sampled as previously described (see Example 3) over the 3 hour reaction period. After 30 minutes, the product, MOB-3', constituted 88% w/w of the nucleoside present and the AMBU content was <2%. Over the subsequent 2½ hours no further reaction occurred. The reaction mixture was cooled and the coloured solid present was filtered off. Deionised water (936.4 g) was then added to the filtrate, which precipitated out the product. The off-white solid was filtered off and washed with ice cold methanol (42.2 g). The product was then dried in a vacuum oven to give an off-white solid (10.66 g). This was assayed by HPLC as 95.8% pure, i.e. a reaction yield of 6.4%.

The aqueous filtrate obtained after removing the precipitated product was then treated in the following way. The filtrate was neutralised by adding calcium carbonate (89.7 g), and ethyl acetate (534.4 g) was then added. The slurry was then filtered to remove calcium fluoride and unreacted calcium carbonate. The filtrate was then phase separated and the separated organic phase was stripped on a rotary evaporator. The sticky solid obtained was treated with methanol, and filtered. The product obtained was dried to given an off-white solid (0.95 g). This was assayed by HPLC at 96.0% w/w, thus representing a further reaction yield of 4.3%.

The overall yield was thus 50.7%.

EXAMPLE 5—The Preparation of 2',3'-Dideoxy-3'-fluoro-5'-(4-methoxybenzoyl) uridine (MOB-3,) in the presence of iron (III) acetylacetonate Into a 1 litre mechanically stirred, monel autoclave, was charged, in the manner previously described (see Example 3), 2',3'-anhydro-5'-O-(4-methoxybenzoyl)uridine (AMBU) (51.64 g, 0.150 moles), iron (III) acetylacetonate (51.04 g, 0.145 moles), 1,4-dioxane (783.34 g, 8.90 moles) and anhydrous hydrogen fluoride (20.88 g, 1.044 moles). The stirred mixture was heated to 95° C. in 30 minutes and held at this temperature for a further 2 hours with stirring. The reaction mixture was then filtered through a basket centrifuge to remove solid residues.

Meanwhile into a 2 litre, mechanically stirred, stainless steel autoclave, was charged in the same manner 2',3'-anhydro-5'-O-(4-methoxybenzoyl)uridine (AMBU)(101.76 g, 0.296 moles), iron (III) acetylacetonate (102.84 g, 0.291 moles), 1,4-dioxane (1569.60 g., 17.84 mols) and anhydrous hydrogen fluoride (40.68 g, 2.034 moles). The stirred mixture was again heated to 95° C. in 30 minutes and held at this temperature, with stirring, for a further 2 hours. The mixture was then cooled and the solids present were filtered off as before. The filtrates from the two separate autoclave runs were combined. Spray dried potassium fluoride (501.1 g, 8.62 mole) was then added, with stirring. The inorganic solids were removed by filtration, and the reaction mixture was evaporated on a rotary evaporator to ca. 250 ml (311 g). Deionised water (ca. 930 g) was then added. The precipitated product was filtered off on a Büchner funnel, washed with water (ca. 100 ml) and then with ice cold methanol (ca. 200 ml). The dried solid (148.75 g) assayed as ca. 85% by HPLC. It was re-washed with hot water (ca. 100 ml), filtered and dried. The re-washed and dried solid (118.5 g) assayed as 97.9% w/w by HPLC, i.e. a reaction yield of 71.1%.

EXAMPLE 6—2',3'-Dideoxy-3,-fluorouridine (FDDU)

Into a 5 litre 3 neck round bottom flask fitted with a mechanical stirrer, thermocouple pocket and calcium chloride drying tube were added 2',3'-dideoxy-3'-fluoro-5'-(4-methoxybenzoyl) uridine (73.3 g of 89.1%; 73.9 g of 92.9%; 11.4 g of 89.4%; 0.396 mole) and methanol (710 ml). Into the stirring slurry was added a solution of sodium hydroxide (17.6 g, 0.44 mole) in methanol (225 ml). After ca. 5 minutes a clear yellow solution was obtained, which was stirred for a further 90 minutes at ambient temperature (20° C.). Water (2880 g) was added, leading to the precipitation of methyl p-methoxybenzoate. After acidifying the mixture to pH 2 with concentrated hydrochloric acid (46.6 g 0.452 mole), the MeMOB was removed by filtration through a sinter funnel. The filtrate was split into two portions, and each portion washed with toluene (1×100 ml). The combined toluene extracts were used to dissolve the MeMOB filter cake, leaving a small quantity of white solid which was dissolved in hot water (50 ml), and added to the washed filtrate. The filtrate was concentrated by rotary evaporation until solid began to appear. After removal from the rotary evaporator, the flask contents were warmed until the solid redissolved, and then left to cool and crystallise. Filtration and drying gave crop 1 of FDDU (94.4 g of 96.4% purity by hplc assay, 90.1% yield). Further evaporation and cooling gave a second crystal crop (6.2 g of 88.2% purity, 6.1% yield).

EXAMPLES 7 TO 13

Proceeding generally in the manner described in Example 4, but with the variations noted in the Table below, AMBU was reacted with hydrogen fluoride in the presence of an organo-iron compound for 2 hours at a reaction temperature of 90° C. The yield of the desired product obtained was as stated in the Table.

| | Quantities of Reagents (g.)* | | | | |
|---|---|---|---|---|---|
| Ex. | Iron Compound | AMBU | HF | Dioxane | Iron Cmpd | Yield % |
| 7 | Fe(III)actylacetonate | 23.4 | 9.5 | 391.4 | 25.9 | 73.2 |
| 8 | Fe(III)tris(t-butyl-acetoacetate) | 24.0 | 10.0 | 403.9 | 39.8 | 76.5 |

-continued

| Iron Ex. Compound | Quantities of Reagents (g.)* | | | | |
|---|---|---|---|---|---|
| | AMBU | HF | Dioxane | Iron Cmpd | Yield % |
| 9 Fe(III)tris(benzoyl-acetonate) | 21.8 | 9.0 | 364.3 | 36.2 | 77.3 |
| 10 Fe(III)tris(dibenzoyl-methonate) | 23.7 | 9.7 | 392.2 | 52.8 | 67.0 |
| 11 Fe(III)tris(propionate) | 23.7 | 9.2 | 386.7 | 20.6 | 50.3 |
| 12 Fe(III)tris(2-ethyl-butyrate) | 24.3 | 9.1 | 389.4 | 29.3 | 54.5 |
| 13 Fe(III)tris(neo-decanoate) | 24.2 | 9.73 | 395.2 | 43.1 | 62.9 |

*In general, the molar ratios used per mole of AMBU were:
HF         6.5
Dioxane    61.0
Iron Compound    1

We claim:

1. Process for the preparation of the 2',3'-dideoxy-3'-fluorouridine nucleoside of formula:

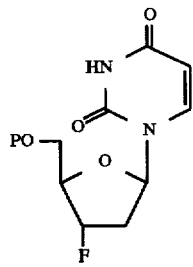

(I)

where P is hydrogen or a hydroxy-protecting group, which comprises reacting an anhydronucleoside of formula:

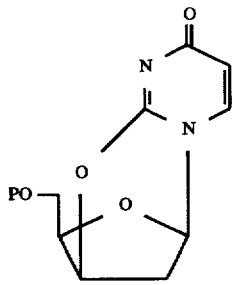

(II)

where P is as hereinbefore defined, with hydrogen fluoride under anhydrous conditions in the presence of an organo-iron (III) compound of formula:

$FeY_mZ_n$ (III)

where Y is a monodentate ligand, Z is a bidentate ligand, and m and n are each zero or positive integers such that (m+2n) =6, and optionally replacing a hydroxy-protecting group P by hydrogen.

2. Process according to claim 1 in which P is 4-methoxybenzoyl, 4-nitrobenzoyl, triphenylmethyl, acetyl, pivaloyl, trimethylsilyl or methanesulphonyl.

3. Process according to claim 1 in which the anhydronucleoside starting material is 2,3'-anhydro-5'-O-(4-methoxybenzoyl)uridine.

4. Process according to claim 1 wherein, Y is halogen or alkoxy of 1 to 4 carbon atoms which may be halogenated, and Z is a carboxylato radical derived from an alkanoic acid of up to 12 carbon atoms or a β-diketo residue of a compound of formula R'-COCH$_2$CO-R", where R' is alkyl or haloalkyl of 1 to 4 carbon atoms and R" is hydrogen, hydroxy, alkoxy of 1 to 4 carbon atoms, br alkyl or haloalkyl of 1 to 4 carbon atoms.

5. Process according to claim 4 in which m is O, n is 3 and Z is a β-diketo residue.

6. Process according to claim 5 in which Z is acetylacetonato.

7. Process according to claim 1 wherein the reaction is carried out in the presence of an inert organic solvent.

8. Process according to claim 7 in which said solvent is 1,4-dioxane, tetrahydrofuran, 1,2-dimethoxy-ethane, or bis (2-methoxyethyl)ether.

9. Process according to claim 1 wherein 2 to 20 moles of hydrogen fluoride are used per mole of anhydronucleoside starting material.

10. Process according to claim 1 wherein 0.5 to 2.0 moles of said organo-iron compound are used per mole of the anhydronucleoside starting material.

11. Process according to claim 1 wherein the reaction is operated at 50° C. to 150° C. under autogenous pressure.

12. 2,3'-Anhydro-5'-(4-methoxybenzoyl)-2'-deoxyuridine.

13. 2',3'-Dideoxy-3'-fluoro-5'-(4-methoxybenzoyl)-uridine.

14. A nucleoside of formula:

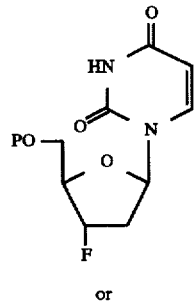

(I)

or

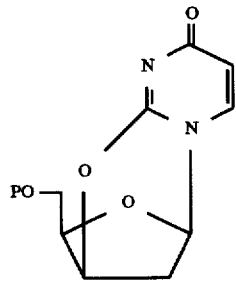

(II)

in which P is branched chain alkanoyl of 4 to 6 carbon atoms, 1- or 2-naphthoyl, or benzoyl substituted by alkoxy of 1 to 4 carbon atoms or by 1 or 2 nitro radicals.

15. A nucleoside as claimed in claim 14 in which P is pivaloyl, 4-methoxybenzoyl, 4-nitrobenzoyl, 3,5-dinitrobenzoyl or 2-naphthoyl.

* * * * *